(12) United States Patent
Gogarty et al.

(10) Patent No.: US 10,318,024 B2
(45) Date of Patent: Jun. 11, 2019

(54) MECHANICAL OPTICAL POINTER

(71) Applicant: ORTHOsoft, Inc., Montreal (CA)

(72) Inventors: Emily Gogarty, Montreal (CA); Pierre Couture, Montreal (CA)

(73) Assignee: ORTHOsoft, Inc., Montreal (CA)

( * ) Notice: Subject to any disclaimer, the term of this patent is extended or adjusted under 35 U.S.C. 154(b) by 0 days.

(21) Appl. No.: 15/716,873

(22) Filed: Sep. 27, 2017

(65) Prior Publication Data

US 2018/0107291 A1 Apr. 19, 2018

Related U.S. Application Data

(60) Provisional application No. 62/408,516, filed on Oct. 14, 2016.

(51) Int. Cl.
*G06F 3/0354* (2013.01)
*A61B 34/20* (2016.01)
*G06F 3/03* (2006.01)
*A61B 90/00* (2016.01)

(52) U.S. Cl.
CPC .......... *G06F 3/03545* (2013.01); *A61B 34/20* (2016.02); *G06F 3/0304* (2013.01); *A61B 90/39* (2016.02); *A61B 2034/2055* (2016.02); *A61B 2034/2068* (2016.02); *A61B 2090/0811* (2016.02); *A61B 2090/371* (2016.02); *A61B 2090/3983* (2016.02)

(58) Field of Classification Search
None
See application file for complete search history.

(56) References Cited

U.S. PATENT DOCUMENTS

| 7,392,076 | B2 | 6/2008 | Moctezuma De La Barrera |
| 7,643,862 | B2* | 1/2010 | Schoenefeld .......... A61B 90/36 600/407 |
| 7,780,681 | B2 | 8/2010 | Sarin et al. |
| 7,840,256 | B2* | 11/2010 | Lakin ..................... A61B 34/20 408/147 |
| 8,238,631 | B2 | 8/2012 | Hartmann et al. |
| 9,179,984 | B2* | 11/2015 | Teichman .............. A61B 90/39 |

FOREIGN PATENT DOCUMENTS

EP 1948062 A2 7/2008

OTHER PUBLICATIONS

"International Application Serial No. PCT/CA2017/051215, International Search Report dated Jan. 9, 2018", 5 pgs.
"International Application Serial No. PCT/CA2017/051215, Written Opinion dated Jan. 9, 2018", 6 pgs.

* cited by examiner

*Primary Examiner* — Kenneth B Lee, Jr.
(74) *Attorney, Agent, or Firm* — Schwegman Lundberg & Woessner, P.A.

(57) ABSTRACT

Embodiments of a system and method for digitizing locations within a coordinate system are generally described herein. A device may include a sleeve including a sleeve tracking marker and a tracked probe portion including an array of tracking markers and a probe tip. Movement of the probe tip relative to the sleeve between at least a first position and a second position may be monitored by tracking the sleeve tracking marker relative to at least one tracking marker of the array of tracking markers.

20 Claims, 4 Drawing Sheets

MECHANICAL OPTICAL POINTER

CLAIM OF PRIORITY

This application claims the benefit of U.S. Provisional Patent Application Ser. No. 62/408,516, filed on Oct. 14, 2016, the benefit of priority of which is claimed hereby, and which is incorporated by reference herein in its entirety.

BACKGROUND

When performing surgery it is sometimes useful to plan certain aspects of the surgery. For example, if bone cuts or implants are to be used in a surgery, a surgeon may want to plan out where to make the bone cuts or place the implants. Using imaging technology and a pointer device, specific locations may be mapped preoperatively or intraoperatively (during surgery). However, devices used to digitize the locations may be expensive, cumbersome to use, require two-handed operation, or require a separate activation device, such as a user interface.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Tracked or navigated pointer devices and the methods of use of pointer devices are described herein. A pointer device may be used to select specific locations, such as on a bone or other target object and map the specific locations within a virtual coordinate system generated by a surgical tracking or navigation system. An optical navigation system, for example, may be used in cooperation with the location digitizer to map the locations on a target bone in a virtual coordinate system. The optical navigation system may track the location digitizer, for example by using a plurality of tracking markers on the location digitizer.

The current inventors recognize, among other things, that activation of digitization of desired locations on a target object can be difficult within a surgical environment. To solve this difficulty, among other benefits, the inventors created a pointer device with a mechanical mechanism that works in conjunction with a tracking system to streamline activation of digitization. In an example, the pointer device may include a mechanical mechanism that may be detected as activated or deactivated, such as by the optical navigation system. When the mechanical mechanism is activated, the optical navigation system may digitize locations, such as locations of a probe tip at a distal end of the pointer device. Locations of the probe tip when the mechanical mechanism is deactivated may be ignored by the optical navigation system. The pointer device may include an array of tracking markers, including tracking markers on a proximal end of the pointer device. A tracking marker may be included on the mechanical sleeve mechanism that moves relative to the remaining tracking markers upon activation of the pointer device. The optical navigation system may track the array of tracking markers and the tracking marker on the mechanical mechanism to determine whether the mechanical mechanism is activated or deactivated. For example, movement of the mechanical mechanism may be used to activate the mechanical mechanism. The movement may be detected by the optical navigation system my determining a location of the tracking marker on the mechanical mechanism with respect to locations of the tracking markers in the array. In an example, systems and methods for tracking objects and digitizing locations in a coordinate system are described herein. Locations of the various tracking markers may be determined within the coordinate system. Locations to be digitized, such as locations identified by the probe tip may be determined within the coordinate system.

Figure 1:
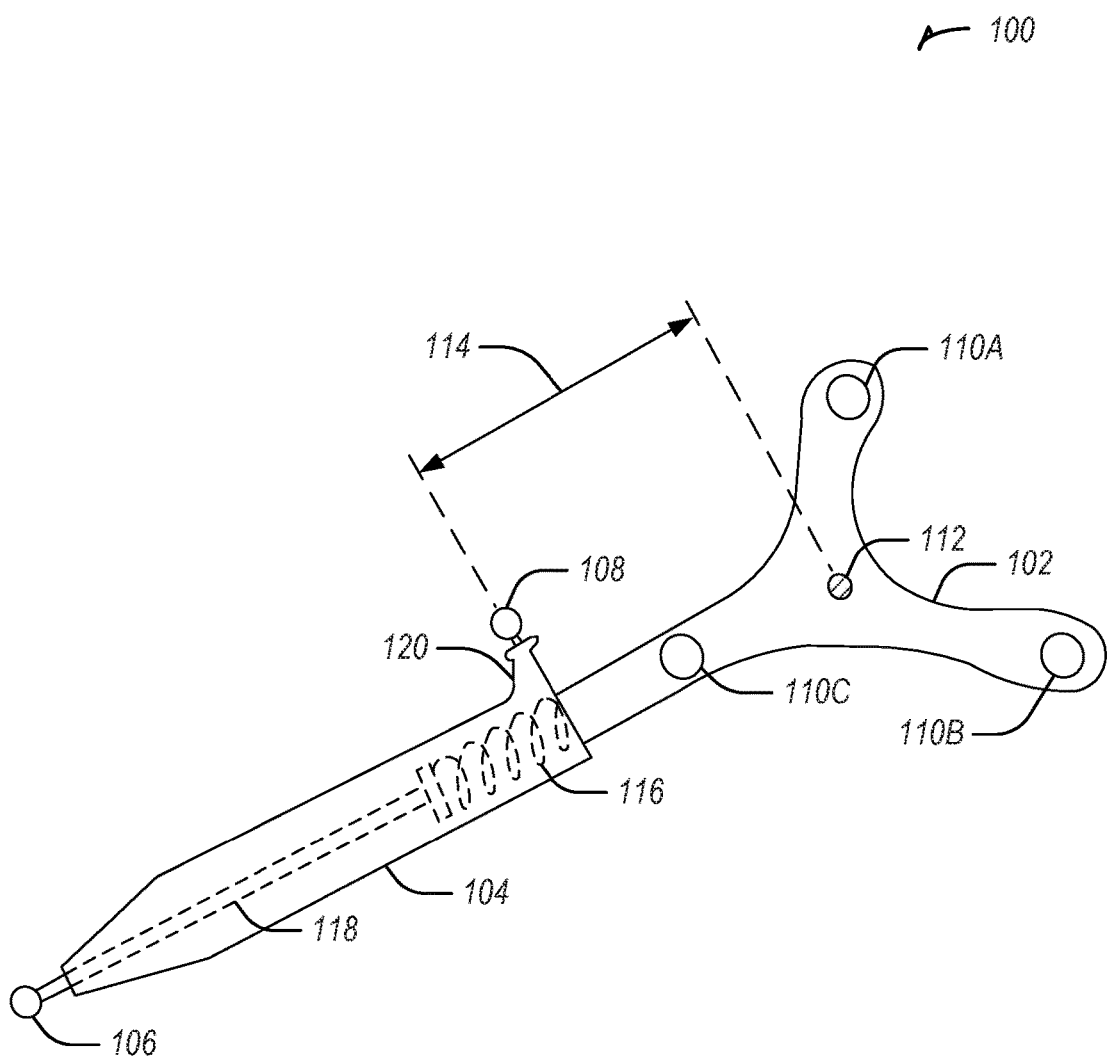
FIG. 1 illustrates a pointer device including a sleeve in accordance with some embodiments.

FIG. 1 illustrates a pointer device 100 including a sleeve 104 in accordance with some embodiments. The pointer device 100 may include a tracked probe 102, including a proximal end. The proximal end may be configured to support an array of tracking markers 110A-110C. In an example, the proximal end may be gripped by a surgeon when digitizing landmarks using the pointer device 100. In another example, the surgeon may grip the sleeve 104 and activate tracking of the pointer device 100, such as by pressing a probe tip 106 against a target object. For example, the probe tip 106 may be pressed with sufficient force to shift location of the tracked probe 102 relative to the sleeve 104.

The array of tracking markers 110A-110C may be identified by an optical navigation system to track a location or orientation of the pointer device 100. For example, the array of tracking markers 110A-110C may be detected by the optical navigation system and locations of the array of tracking markers 110A-110C within a coordinate system may be determined. The tracked probe 102 may include a distal end including the probe tip 106. The locations in the coordinate system may be used to determine where the probe tip 106 is located and that location may be digitized. In an example, the locations include locations on a target object, such as a bone. The locations may be displayed on a user interface with a virtual representation of the target object.

The tracked probe 102 may include an intermediate section 118 adapted to slidably engage the sleeve 104 when disposed within a bore of the sleeve 104. The intermediate section 118 may connect the probe tip 106 with the proximal portion of the tracked probe 102. The intermediate section 118 may be at least partially or fully radially surrounded by the sleeve 104. In an example, when the sleeve 104 slides along the intermediate section 118, the intermediate section 118 may provide friction against the bore, such as to prevent accidental movement. In another example, the sleeve 104 may slide without the intermediate section 118 coming into contact with the bore.

In an example, the tracked probe 102 includes an intermediate point 112, which may be used as a fixed point for determining a distance 114 to a tracking marker (e.g., 110A-110C or 108). A location of the intermediate point 112 may be determined by triangulating or otherwise inferring the location from the array of tracking markers 110A-110C. The intermediate point 112 may be compared to a sleeve tracking marker 108 to determine a change in a distance between the intermediate point 112 and the sleeve tracking marker 108. In an example, a condition for digitizing locations with the probe tip 106 may include determining whether the change has caused the distance to transgress a threshold. The intermediate point 112 is used herein as a convenience for describing the relative movement of the sleeve 104 (represented by sleeve tracking marker 108) and the tracked probe 102 (represented by tracking markers 110A-110C), but is not inherently necessary for the described device to function. The location of each tracking marker of tracking markers 110A-110C is known in reference to the tracked probe 102, and detecting location of any two may be sufficient to determine location of the tracked probe 102. Detection of the location of all three tracking markers 110A-110C may be used to positively calculate the location and orientation of the tracked probe 102, without necessarily calculating intermediate point 112.

The sleeve 104 may include a distal end, a proximal end, and a bore along a longitudinal axis between the distal end and the proximal end. In an example, the sleeve 104 may be disposable. In an example, the sleeve 104 may comprise two or more independent components configured to couple together, such as around a portion of the pointer device 100 (e.g., the intermediate section 118). The two or more independent components may be joined to create a bore. For example, if the sleeve 104 is disposable, the two or more independent components may be fitted over the tracked probe 102 and then discarded after use. In another example, the probe tip 106 may be configured to pass through the sleeve 104 during assembly (e.g., through the bore) such that the sleeve 104 may slide on to the tracked probe 102. In yet another example, the probe tip 106 may be configured to detach from the tracked probe 102, such as to allow the sleeve 104 to slide onto the tracked probe 102 (e.g., the intermediate section 118). After the sleeve 104 is coupled to the tracked probe 102, the probe tip 106 may be attached (e.g., in an example, the probe tip 106 may be disposable) or reattached. Attaching or reattaching the probe tip 106 may secure the sleeve 104 on the tracked probe 102, such that the sleeve 104 does not slide off of the tracked probe 102.

The sleeve 104 may include the sleeve tracking marker 108 affixed adjacent to the proximal end. The sleeve tracking marker 108 may be a reflective marker, such as one identifiable by an optical navigation system. The optical navigation system may detect a position of the sleeve tracking marker 108, such as within a coordinate system or relative to one or more tracking markers of the array of tracking markers 110A-110C. In an example, the position of the sleeve tracking marker 108 may be used to determine a distance, such as a distance to one or more tracking markers of the array of tracking markers or a distance to the intermediate point 112. The distance may be used to determine whether a threshold has been transgressed. For example, when the distance exceeds a threshold or falls below a threshold, a location of the probe tip 106 may be digitized or may be ignored. In an example, movement of the probe tip 106 relative to the sleeve 104 between at least a first position and a second position may be monitored, such as by the optical navigation system. The movement between the first position and the second position may be monitored by tracking the sleeve tracking marker 108. In an example, a distance from the sleeve tracking marker 108 to a reference point may be tracked over a period of time, such as at intervals (e.g., every millisecond, every second, etc.). When the distance is determined to transgress a threshold during a period of time, multiple locations of the probe tip 106 may be digitized, such as to create a set of locations, a curve of locations (which may be smoothed out digitally), or an area of locations (e.g., if a region is enclosed by the locations during the period of time, the enclosed region may be deemed a digitized area).

In an example, the sleeve tracking marker 108 may be affixed to a mechanism 120, such as a mechanical mechanism. The mechanism 120 may be a trigger mechanism, such that when pulled, the sleeve tracking marker 108 is moved towards the proximal end of the tracked probe 102. The mechanism 120 may be activated by a surgeon pulling the mechanism 120 towards the proximal end of the tracked probe 102, thus decreasing the distance between the sleeve tracking marker 108 and the intermediate point 112 or at least one of the tracking markers of the array of tracking markers. The optical navigation system may determine that the distance has changed and that the distance has transgressed a threshold in response to the mechanism 120 being activated.

In an example, the sleeve tracking marker 108 may replace the tracking marker 110C in an array of tracking markers to create a new array of tracking markers including the tracking markers 110A and 110B. For example, an optical navigation system may determine that the sleeve tracking marker 108 with the tracking markers 110A and 110B create the new array of tracking markers. In response to detecting the new array of tracking markers (e.g., that the sleeve tracking marker 108 has replaced the tracking marker 110C), the probe tip 106 may be activated for digitizing locations (e.g., on a target object). In another example, the sleeve tracking marker 108 may be detected as part of a new array of tracking markers (e.g., along with tracking markers 110A and 110B), and the new array of tracking markers may be compared with the array of tracking markers 110A-110C. For example, a first triangulated location (e.g., the intermediate point 112) for the array of tracking markers 110A-110C may be compared with a second triangulated location for the new array of tracking markers. A distance between the first triangulated location and the second triangulated location may be determined, and that distance may be compared with a threshold to determine if that distance has transgressed the threshold.

In an example, a distance (e.g., from the sleeve tracking marker 108 to one or more other tracking markers, the probe tip 106, the intermediate point 112, between triangulated points, etc.) may be used in a multi-state configuration. A state may correspond with a particular distance. In an example, a first state may be used to identify a location to be digitized is identified, and a second state may be used to delete a digitized location. In another example, states may be sequential including a first state and a second state. For example a first distance transgressing a threshold may correspond with a first state and then a second distance re-transgressing the threshold may correspond with a second state. In another example, the distance may transgress a first threshold corresponding to a first state, and the distance may change to transgress a second threshold corresponding to a second state. These states may be used to sequentially identify locations to be digitized (e.g., expected sequential points such as a head center, a mechanical axis entry, a medial epicondyle, etc.).

In an example, the mechanism 120 may be triggered to move the sleeve tracking marker 108 a distance, such as halfway, which may be indicated by a change in resistance or physical, audible, or haptic feedback. The halfway position (or a third of the way, or a quarter, etc.) may be used for a first digitized location (e.g., a head center), and a full distance may be used for a second digitized location (e.g., a mechanical axis entry). In an example, rapid changes in distance may be used to indicate changes to previously registered digital landmarks. For example, if the distance transgresses a threshold twice within a predetermined period of time (e.g., within a second), a previously digitized landmark may be removed from memory of a system. For example, the immediately previously digitized landmark may be deleted from memory. In another example, rapid changes in distance may be used to reset a system (e.g., erase from memory all or a set of previously digitized landmarks).

The sleeve 104 may include an elastic resistance member 116, such as a spring, elastic band, or the like. The elastic resistance member 116 may be used to resist movement of the sleeve 104, such as resisting sliding movement of the sleeve 104 with respect to the intermediate section 118 or resisting movement of the sleeve 104 with respect to the probe tip 106. In an example, resistance provided by the elastic resistance member 116 may be overcome when the mechanism 120 is engaged. For example, when the mechanism 120 is a trigger mechanism and the elastic resistance member 116 is a spring, the trigger mechanism may be pulled to compress the spring, and thus move the sleeve 104 relative to the proximal end of the tracked probe 102.

In an example, other moveable components may be used instead of the sleeve 104. For example, a track, a lever, or another mechanism moveable relative to a portion of the tracked probe 102, such as a frame portion or the intermediate section 118, or the probe tip 106.

Figure 2:
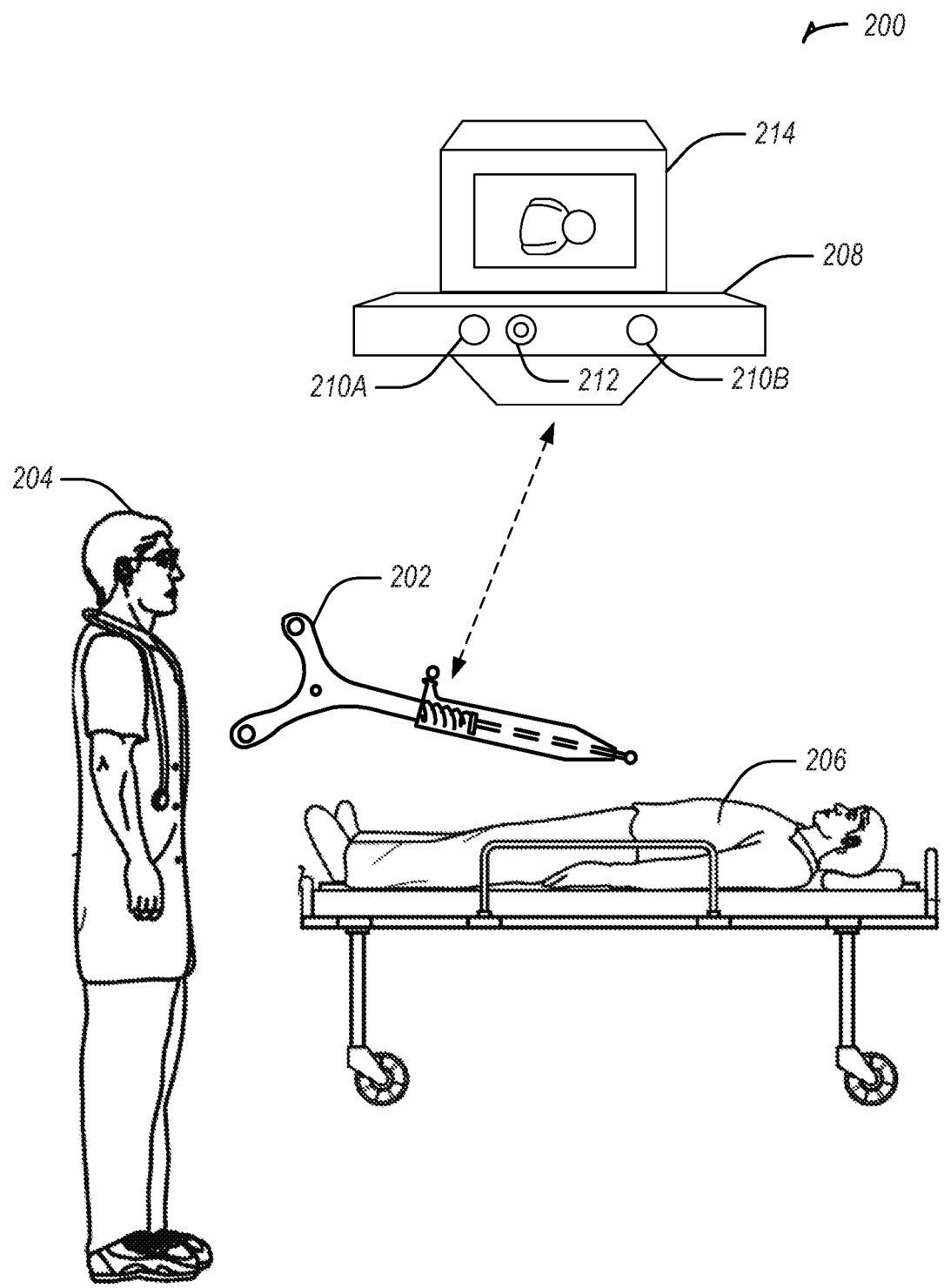
FIG. 2 illustrates a system for digitizing locations within a coordinate system in accordance with some embodiments.

FIG. 2 illustrates a system 200 for digitizing locations within a coordinate system in accordance with some embodiments. The system 200 includes a pointer device 202 and an optical navigation system 208. The system 200 may be used by a surgeon 204 to digitize locations within a coordinate system, such as locations on a patient 206. The optical navigation system 208 may track the pointer device 202 as the pointer device 202 moves within the coordinate system. The pointer device 202 may include aspects described above with respect to FIG. 1, such as an array of tracking markers, a sleeve tracking marker, and a mechanism for activating a probe tip of the pointer device 202. The optical navigation system 208 may track the array of tracking markers and the sleeve tracking marker. In an example, the optical navigation system 208 may determine a distance from the sleeve tracking marker to one or more of the array of tracking markers or to an intermediate point on the pointer device 202. The optical navigation system 208 may detect that the distance has changed. In response to determining that the distance has changed, the optical navigation system 208 may determine whether the distance has transgressed a threshold, and if it has, register a location (e.g., a location of the probe tip on the pointer device 202).

The optical navigation system 208 may include a plurality of cameras 210A-210B, an infrared light source 212, and optionally a display 214. The plurality of cameras 210A-210B may detect infrared light originating at the infrared light source 212 and reflected off a tracking marker (e.g., the array of tracking markers or the sleeve tracking marker). In an example, the plurality of cameras 210A-210B may include a visible light filter. In another example, the optical navigation system 208 may include a camera to capture visible light, such as the surgical field to display on the display 214. In an example, the display 214 may be used to show a virtual representation of a target object, digitized locations, or the pointer device 202.

The optical navigation system 208 may include a processor and memory, may be connected to a server or cloud service, or may be connected with a database. Processing of information, such as digitizing landmarks, determining whether a distance involving the sleeve tracking marker, or detecting that the distance has changed (e.g., whether a threshold has been transgressed) may be done by the processor, the server the cloud service, etc.

Figure 3:
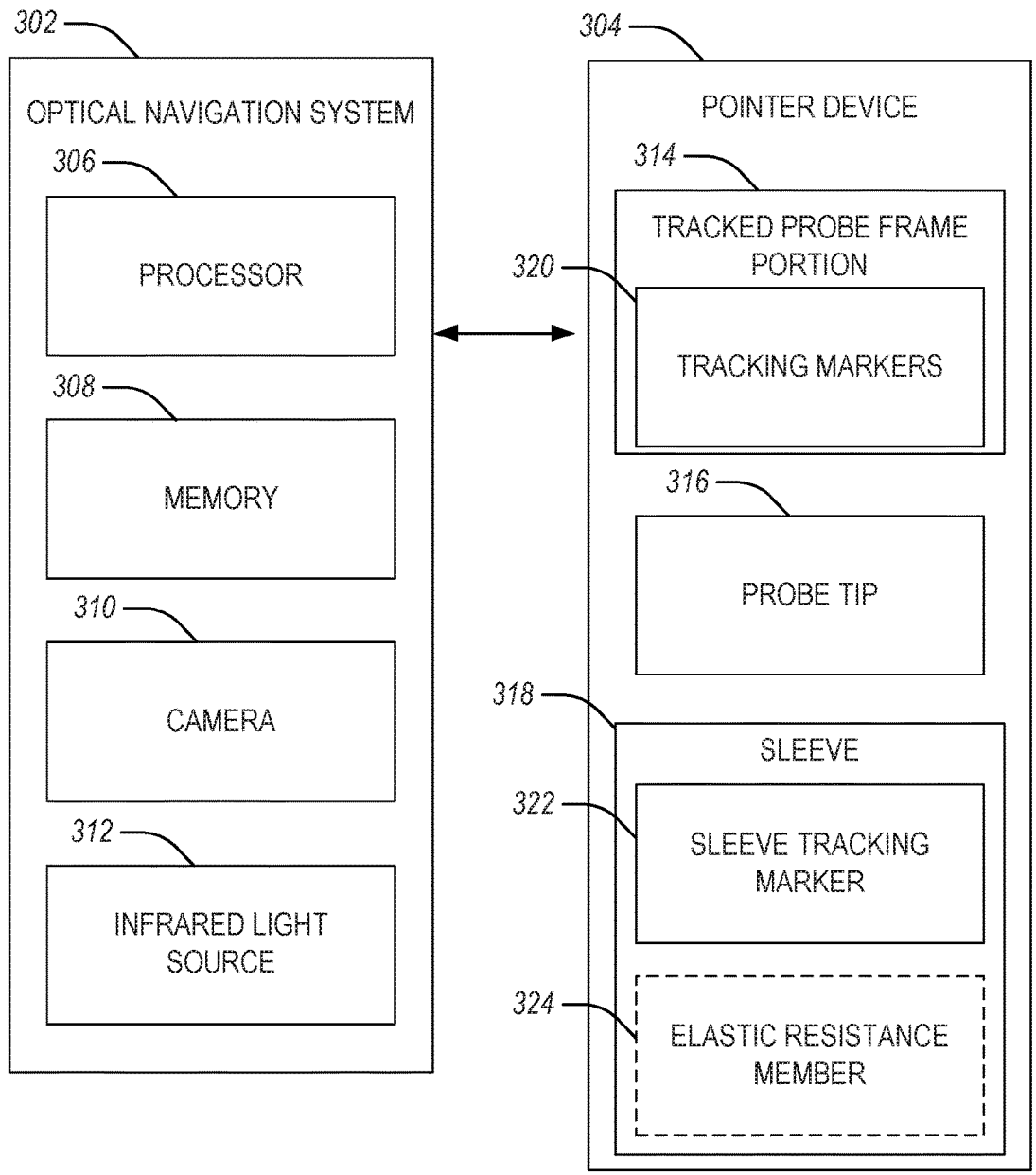
FIG. 3 illustrates a system for tracking objects in a coordinate system in accordance with some embodiments.

FIG. 3 illustrates a system 300 for tracking objects in a coordinate system in accordance with some embodiments. The system 300 includes an optical navigation system 302 and a pointer device 304. The optical navigation system 302 includes a processor 306, memory 308, at least one camera 310, and an infrared light source 312. The at least one camera 310 may be used to detect infrared light, such as light reflected off of tracking markers, the light originating from the infrared light source 312.

The pointer device 304 includes a tracked probe frame portion 314, a probe tip 316, and a sleeve 318. The probe tip 316 may be disposed on a distal end of the pointer device 304. The tracked probe frame portion 314 includes an array of tracking markers 320. The sleeve 318 includes a sleeve tracking marker 322. The sleeve 318 may include a distal end, a proximal end, and a bore along a longitudinal axis between the distal end and the proximal end. The pointer device 304 may include an intermediate section adapted to slidably engage the sleeve 318, such as when the intermediate section is disposed within the bore of the sleeve 318.

The memory 308 may be used to store instructions, which when executed by the processor 306 cause the processor 306 to perform operations. The processor 306 may be used to determine movement of the probe tip 316 relative to the sleeve 318 between at least a first position and a second position. The movement may be monitored by tracking the sleeve tracking marker 322 relative to at least one tracking marker of the array of tracking markers 320, the probe tip 316, or an intermediate point on the pointer device 304 (e.g., on the tracked probe frame portion 314). In an example, movement of the probe tip 316 into the second position may indicate a location to be digitized at the probe tip 316 through transgressing a threshold distance between the sleeve tracking marker 322 and the at least one tracking marker of the array of tracking markers 320, the probe tip 316, or the intermediate point.

In an example, the sleeve 318 is disposable. For example, the pointer device 304 may be used in multiple surgeries, replacing the sleeve 318 each time. The sleeve may optionally include an elastic resistance member 324. The elastic resistance member 324 may be disposed within the bore and may provide resistance to movement of the sleeve 318 in a direction along the bore (e.g., sliding along the intermediate section). In an example, the elastic resistance member 324 may include a spring, an elastic band, or the like. The sleeve 318 may be configured to receive a force that causes the elastic resistance member 324 to compress or relax. The force may decrease a distance between the sleeve tracking marker 322 and the at least one tracking marker of the array of tracking markers 320, the probe tip 316, or the intermediate point. In an example, the sleeve 318 may include a mechanism to receive the force, such as a trigger mechanism or other mechanical mechanism.

In an example, the processor 306 may be used to receive information from the camera 310. The camera 310 may include two or more cameras, including cameras with a visible light filter (e.g., to allow infrared light through). The processor 306 may determine whether a distance from the sleeve tracking marker 322 to at least one tracking marker of the array of tracking markers 320 has transgressed a threshold. In response to determining that the distance has transgressed the threshold, the processor 306 may register one or more locations of the probe tip 316 of the pointer device 304.

Figure 4:
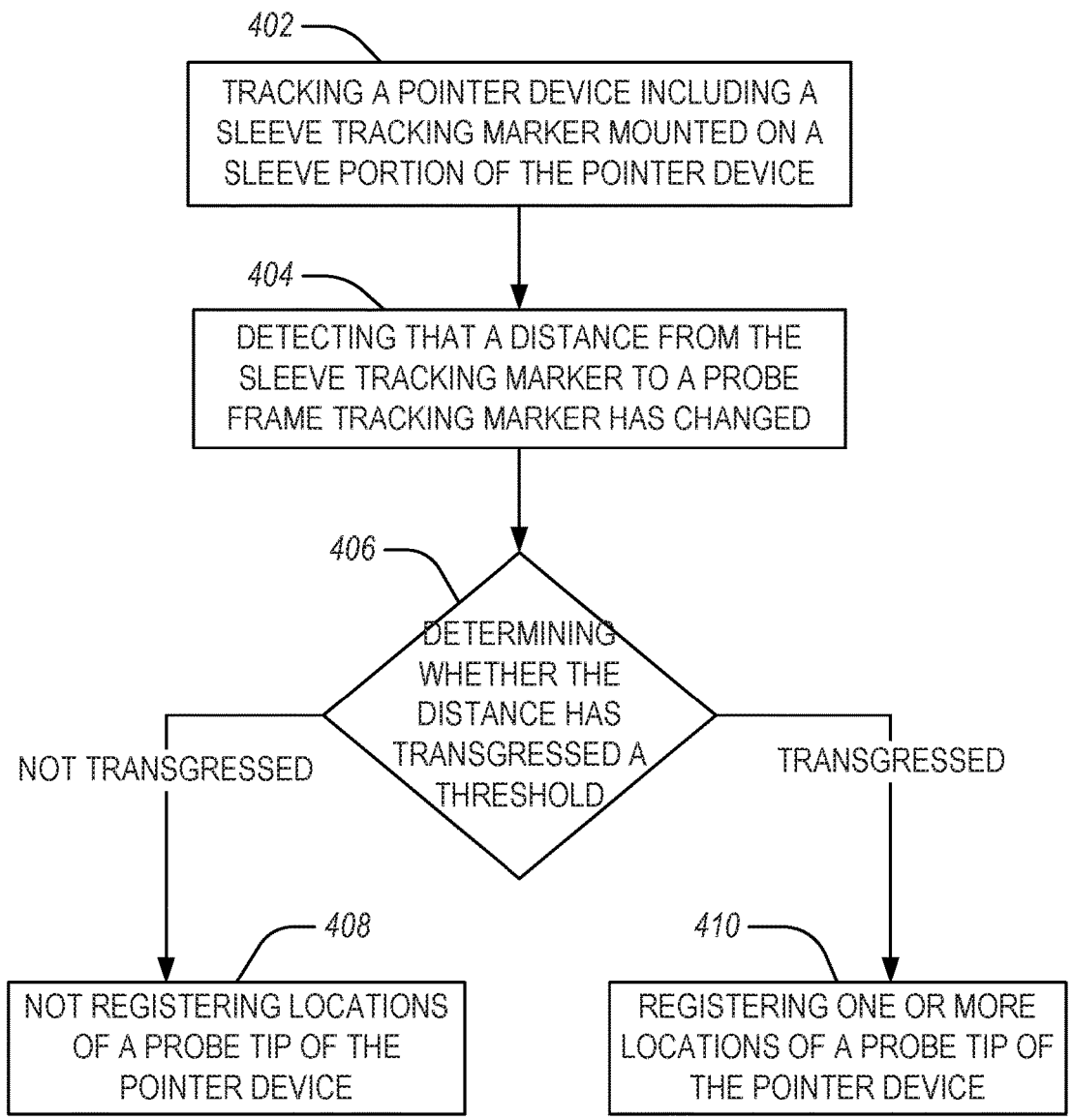
FIG. 4 illustrates a flow chart showing a technique for digitizing locations within a coordinate system in accordance with some embodiments.

FIG. 4 illustrates a flow chart showing a technique 400 for digitizing locations within a coordinate system in accordance with some embodiments. The technique 400 includes an operation 402 to track a pointer device including a moveable component tracking marker mounted on a moveable component, such as a sleeve portion, of the pointer device. In another example, the moveable component may include a track, a lever, or another mechanism moveable relative to a portion of the pointer device, such as a frame portion. The operation 402 may be performed using an optical navigation system. The pointer device may include an array of tracking markers mounted on a tracked probe frame portion of the pointer device.

The technique 400 includes an operation 404 to detect, such as using the optical navigation system, that a distance from the moveable component tracking marker to a probe frame tracking marker has changed, for example a probe frame tracking marker of the array of tracking markers. In an example, detecting that the distance has changed may include detecting that the distance from the moveable component tracking marker to all tracking markers of the array of tracking markers has changed.

The technique 400 includes a decision operation 406 to determine whether the distance from the moveable component tracking marker to the probe frame tracking marker has transgressed a threshold. The operation 406 may include determining an intermediate point on the tracked probe frame portion and determining a distance from the intermediate point to the moveable component tracking marker. The intermediate point may be determined by triangulating distances from at least three tracking markers of the array of tracking markers. In an example, determining whether the distance has transgressed the threshold includes determining that the distance has fallen below the threshold due to movement of the moveable component (e.g., the sleeve portion) of the pointer device.

The technique 400 includes an operation 408 to, in response to determining that the distance has not transgressed the threshold, not register locations of a probe tip of the pointer device or cease registering locations of the probe tip. The technique 400 includes an operation 410 to, in response to determining that the distance has transgressed the threshold, registering one or more locations of the probe tip of the pointer device.

The technique 400 may include an operation to determine that the distance has transgressed the threshold for a period of time. The technique 400 may include grouping the one or more locations of the probe tip of the pointer device registered during the period of time. For example, the one or more locations may be grouped as a curve, area, series of locations, or the like.

In an example, the moveable component (e.g., the sleeve portion) of the pointer device may be disposable. The technique 400 may include determining an initial distance from the moveable component tracking marker to one or more or each of the array of tracking markers. The initial distance may be based on an installed position of the moveable component (e.g., the sleeve portion) of the pointer device.

In an example the term "machine readable medium" may include a single medium or multiple media (e.g., a centralized or distributed database, or associated caches and servers) configured to store one or more instructions. The term "machine readable medium" may include any medium that is capable of storing, encoding, or carrying instructions for execution by a machine and that cause the machine to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the detailed description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled. The above detailed description includes references to the accompanying drawings, which form a part of the detailed description. The drawings show, by way of illustration, specific embodiments in which the invention can be practiced.

What is claimed is:

1. A pointer device for digitizing locations within a coordinate system, the pointer device comprising:
   a sleeve including a distal end, a proximal end, and a bore along a longitudinal axis between the distal end and the proximal end, the sleeve including a sleeve tracking marker affixed adjacent to the proximal end; and
   a tracked probe including a proximal end configured to support an array of tracking markers, a distal end including a probe tip, and an intermediate section adapted to slidably engage the sleeve when disposed within the bore;
   wherein movement of the probe tip relative to the sleeve between at least a first position and a second position can be monitored by tracking the sleeve tracking marker relative to at least one tracking marker of the array of tracking markers, wherein a distance between the sleeve tracking marker and the at least one tracking marker of the array of tracking markers is shorter along the longitudinal axis when the probe tip is at the second position than when the probe tip is at the first position.

2. The pointer device of claim 1, wherein movement of the probe tip into the second position indicates a location to be digitized at the probe tip through transgressing a threshold distance between the sleeve tracking marker and the at least one tracking marker of the array of tracking markers.

3. The pointer device of claim 1, wherein the sleeve is disposable.

4. The pointer device of claim 1, wherein the sleeve includes an elastic resistance member disposed within the bore, the elastic resistance member providing resistance to movement of the sleeve in a direction along the bore.

5. The pointer device of claim 4, wherein the elastic resistance member is a spring.

6. The pointer device of claim 4, wherein the sleeve is configured to receive a force that causes the elastic resistance member to compress and decreases a distance between the sleeve tracking marker and the at least one tracking marker of the array of tracking markers.

7. The pointer device of claim 6, wherein the sleeve includes a trigger mechanism to receive the force.

8. A method for tracking objects in a coordinate system, the method comprising:
    tracking, using an optical navigation system, a pointer device including a sleeve tracking marker mounted on a sleeve portion of the pointer device and an array of tracking markers mounted on a tracked probe frame portion of the pointer device;
    detecting, using the optical navigation system, that a distance from the sleeve tracking marker to at least one tracking marker of the array of tracking markers has changed;
    determining whether the distance from the sleeve tracking marker to the at least one tracking marker has transgressed a threshold; and
    registering, in response to determining that the threshold has been transgressed, one or more locations of a probe tip of the pointer device.

9. The method of claim 8, wherein determining whether the distance has transgressed the threshold includes determining an intermediate point on the tracked probe frame portion, and determining a distance from the intermediate point to the sleeve tracking marker.

10. The method of claim 9, wherein determining the intermediate point includes triangulating distances from at least three tracking markers of the array of tracking markers.

11. The method of claim 8, wherein detecting that the distance from the sleeve tracking marker to at least one tracking marker of the array of tracking markers has changed includes detecting that the distance from the sleeve tracking marker to all tracking markers of the array of tracking markers has changed.

12. The method of claim 8, wherein determining whether the distance from the optical tracker to the optical marker has transgressed the threshold includes determining that the distance has fallen below the threshold due to movement of the sleeve portion of the pointer device.

13. The method of claim 8, further comprising preventing registration, in response to determining that the threshold has not been transgressed, of locations of the probe tip of the pointer device.

14. The method of claim 8, further comprising:
    determining that the distance has transgressed the threshold for a period of time, and
    grouping the one or more locations of the probe tip of the pointer device registered during the period of time.

15. The method of claim 8, wherein the sleeve portion of the pointer device is disposable and further comprising determining an initial distance from the sleeve tracking marker to each of the array of tracking markers, the initial distance based on an installed position of the sleeve portion of the pointer device.

16. A system for tracking objects in a coordinate system, the system comprising:
    a pointer device including a sleeve with a sleeve tracking marker mounted on the sleeve portion, an array of tracking markers mounted on a tracked probe frame portion of the pointer device, and a probe tip; and
    an optical navigation system including two or more cameras, an infrared light source, and a processor, the processor to:
    receive information from the two or more cameras;
    determine whether a distance from the sleeve tracking marker to at least one tracking marker of the array of tracking markers has transgressed a threshold; and
    register, in response to determining that the threshold has been transgressed, one or more locations of the probe tip of the pointer device.

17. The system of claim 16, wherein the sleeve is disposable.

18. The system of claim 16, wherein the sleeve includes an elastic resistance member, the elastic resistance member providing resistance to sliding movement of the sleeve against the pointer device.

19. The pointer device of claim 18, wherein the elastic resistance member is a spring.

20. The pointer device of claim 18, wherein the sleeve includes a trigger mechanism configured to receive a force that causes the elastic resistance member to compress and decreases a distance between the sleeve tracking marker and the at least one tracking marker of the array of tracking markers.

* * * * *